United States Statutory Invention Registration [19]

[11] Reg. Number: H494

Larrick [43] Published: Jul. 5, 1988

[54] *PSEUDOMONAS AERUGINOSA* TYPE-SPECIFIC MURINE MONOCLONAL ANTIBODIES, THEIR PREPARATION AND USE

[75] Inventor: James W. Larrick, Woodside, Calif.

[73] Assignee: Cetus Corporation, Emeryville, Calif.

[21] Appl. No.: 727,516

[22] Filed: Apr. 26, 1985

[51] Int. Cl.[4] ..... C12N 5/00; A61L 39/40

[52] U.S. Cl. ..... 435/240.26; 530/387; 435/172.2; 435/68; 424/85; 424/87

[56] References Cited

FOREIGN PATENT DOCUMENTS 0101039 2/1984 European Pat. Off. .

OTHER PUBLICATIONS

Cryz et al., *Inf. Imm.* (1983) 40:659–664.
Moody et al., *Infect. Imm.* (1978) 21:905–913.
Kohler and White, *J. Infect. Dis.* (1977) 136:112–116.
Collins et al., *J. of Trauma* (1983) 23: 530–534.
Cryz et al., *Infect. Immun.* (1983) 39: 1072–1079.
Sawada et al., *J. Infect. Dis.* (1984) 150: 570–576.
Hancock et al., *Infect. Immun.* (1982) 37: 166–171.
Mackie et al., *J. Immunol.* (1982) 129: 829–32.

*Primary Examiner*—Teddy S. Gron
*Attorney, Agent, or Firm*—Albert P. Halluin; Janet E. Hasak

[57] ABSTRACT

Serotype-specific murine anti-Pseudomonas monoclonal antibodies which bind to determinants of the cell wall lipopolysaccharides of *P. aeruginosa* are prepared from hybrid cell lines. The antibodies may be of any isotype. These antibodies may be used to treat infections caused by *P. aeruginosa.*

2 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

*PSEUDOMONAS AERUGINOSA* TYPE-SPECIFIC MURINE MONOCLONAL ANTIBODIES, THEIR PREPARATION AND USE

BACKGROUND OF THE INVENTION

This invention relates to the production of mouse monoclonal antibodies which are type specific and directed against *Pseudomonas aeruginosa.*

*Pseudomonas aeruginosa* is a highly virulent pathogen which infects patients receiving immunosuppressive therapy or suffering from severe thermal burns or other serious injuries, cystic fibrosis, or neoplastic diseases. Mortality from *P. aeruginosa* has been reduced as the result of such therapeutic agents as mafenide acetate and silver salts which inhibit bacterial colonization of the burn wound surface, potent antibiotics for treating bacteremia, and barrier isolation to minimize contact of the patient with hospital flora. Such agents, however, have only proved partially successful in controlling the morbidity and mortality associated with Pseudomonas infections.

Recently, researchers have found that specific antibodies constitute a critical immunologic defense mechanism against Pseudomonas disease; therefore, vaccines have been administered to patients in attempts to increase antibody titers in the patients. No non-toxic vaccines have been found to date which are particularly effective against the pathogen.

It is not yet clear what components of *P. aeruginosa* are responsible for its virulence. Many different types of infections are recognized, from acute localized eye infections and chronic lung infections to generalized systemic infections and septicemia. Several lines of evidence, however, suggest that lipopolysaccharide (endotoxin) (LPS) contributes substantially as a pathogenic factor. These include the toxic nature of *P. aeruginosa* LPS (Pennington et al., *Am. J. Med.,* 58, 629–636 (1975)), and the fact that circulating antibodies to LPS are shown to prevent or attenuate some of the adverse effects of LPS in experimental models (Cryz et al., *Infect. Immun.* (1983) 40:659–664; Young et al., *J. Clin. Invest.* (1975) 56:850–861). Pollack et al., *J. Clin. Invest.* (1975) 63:276–286, concluded from their studies that serum antibodies to LPS found in most patients with *P. aeruginosa* septicemia were correlated with patient recovery.

Numerous studies have indicated that immunoglobulin G (IgG) antibody to LPS is protective in experimentally infected animals (Cryz et al., supra; Moody et al., *Infect. Immun.* (1978) 21:905–913), and more so when combined with an antibiotic (Cryz et al., supra). A heptavalent vaccine containing LPS of the seven Fisher-Devlin-Gnabasik immunotypes of *P. aeruginosa* (Fisher et al., *J. Bacteriol.* (1969) 98:833–836) was found to be effective in inducing antibodies in humans. See Kohler and White, *J. Infect. Dis.* (1977) 136:112–116. Attempts to immunize patients at high risk of *P. aeruginosa* infection with this vaccine, however, have been only moderately successful due in part to the potent endotoxin activity of LPS. Local and systemic adverse reactions to endotoxin, including fever, malaise, and pain at the site of injection, can limit vaccine dosage. See Pennington et al., supra.

Collins et al., *J. of Trauma* (1983) 23:530–534 disclose a test of a commercially available human IgG in burned mice for activity against the seven immunotypes of *P. aeruginosa* and an additional strain. The human IgG was not effective against immunotypes 5 and 6 but was protective against immunotypes 1–4 and 7. In addition, Cryz et al., *Infect. Immun.* (1983) 39:1072, and Sawada et al., *J. Infect. Dis.* (1984) 150:570 disclose work suggesting that type-specific anti-*P. aeruginosa* antisera and mouse monoclonal antibodies can reduce the lethality of these bacteria in the burned mouse model. Further, Hancock et al., *Infect. Immun.* (1982) 37:166–171, disclose hybridomas secreting monoclonal antibodies specific for *P. aeruginosa* LPS, and Mackie et al., *J. Immunol.* (1982) 129:829–32 and EP 101,039 disclose monoclonal antibodies against *P. aeruginosa.*

There is a need to develop monoclonal antibodies for passive immunotherapy of patients infected with *P. aeruginosa.*

SUMMARY OF THE INVENTION

Accordingly, the present invention provides a serotype-specific murine anti-Pseudomonas antibody which binds to determinants of the cell wall lipopolysaccharides of *Pseudomonas aeruginosa* and whose population is substantially homogeneous, i.e., the antibody is monoclonal.

Another aspect of the invention herein is a stable, permanent hybrid cell line which produces such antibody and progeny of the cell line.

In addition, the invention relates to compositions for treating infections caused by *Pseudomonas aeruginosa* comprising a therapeutically effective amount of such antibody in association with a pharmaceutically acceptable parenteral vehicle.

In a further aspect, the invention relates to a method for treating a mammalian patient for infections caused by *P. aeruginosa* comprising administering an effective amount of such antibody to the patient parenterally.

The antibodies herein may be successfully utilized for passive immunotherapy against, or prophylaxis of, Pseudomonas infections.

DESCRIPTION OF THE PREFERRED EMBODIMENTS

As used herein the term "cell line" refers to individual cells, harvested cells, and cultures containing cells so long as they are derived from cells of the cell line referred to.

As used herein with respect to hybrid cell lines, the term "progeny" is intended to include all derivatives, issue, and offspring of the cell lines regardless of generation of karyotypic identity.

As used herein with respect to a given antibody, the term "functional equivalent" means an antibody that recognizes the same determinant as and crossblocks the antibody referred to. It is intended to include antibodies of the same or different immunoglobin class and antigen binding fragments (e.g., Fab, $F(ab')_2$, Fv) of the antibody.

As used herein with respect to administering antibody to patients, the term "treat" and conjugates thereof refers to therapy and/or prophylaxis.

As used herein the term "monoclonal antibody" refers to an antibody selected from antibodies whose population is substantially homogeneous, i.e., the individuals of the antibody population are identical except for naturally occurring mutations.

As used herein with respect to characterizing the claimed hybrid cell lines, the terms "permanent" and "stable" mean that the lines remain viable over a prolonged period of time, typically at least about six months, and maintain the ability to produce the specified monoclonal antibody through at least about 50 passages.

As used herein the term "serotype" refers to one of the seven Fisher-Devlin-Gnabasik immunotypes of *P. aeruginosa* described by Fisher et al., *J. Bacteriol.*, 98, 833–836 (1969).

The murine antibodies herein which are specific against one or more of the seven serotypes are monoclonal. While it is preferable to have an antibody directed against all seven serotypes, exemplified herein are antibodies directed against each of serotypes 1–7. Also, the antibodies herein may be any isotype, preferably IgM or IgG. They are made by fusion involving cells of mouse and human origin. These antibodies may be the products of hybridomas synthesized by somatic cell hybridization using a mouse myeloma cell line and a murine cell line producing sufficiently high levels of anti-*P. aeruginosa* serotype-specific antibodies. The latter cell line may be from, e.g., splenocytes. The latter cell lines may be obtained from Balb/c or other strains of mice immunized and boosted with available *P. aeruginosa* vaccine, heat-inactivated *P. aeruginosa* bacteria, or *P. aeruginosa* cell wall or LPS preparations.

One strategy for preparing and identifying hybrids which produce antibodies of the invention follows. Balb/c mice are immunized and boosted with heat-killed *P. aeruginosa* bacteria of each of the seven serotypes.

The spleens are removed and the cells are then fused to a tumor fusion partner consisting of HAT-nonresistant mouse myeloma cells such as SP-2 cells obtainable from ATCC, using the technique described by Kohler and Milstein, *Nature* (1975) 256:495–497. The selection medium is enhanced with hypoxanthine and azaserine to kill unfused mouse myeloma cells and unfused spenocytes. Supernatants from the selected growing hybrid cells are screened by ELISA against bacteria from each serotype and against a heptavalent vaccine. Hybrids which are positive for only one serotype are expanded, and the supernatants are tested in in vitro and in vivo models (such as a burned mouse model). The supernatants containing the antibodies may be immunoblotted on extracted LPS.

The antigen-binding ability of the antibodies herein is evaluated by LPS immunoblots, ELISAs and bacterial binding. Those antibodies which have the ability to block the adverse biological effects of *P. aeruginosa* in mammals regardless of the mechanism involved are preferred.

The hybridomas which produce the antibodies of this invention may be grown in suitable culture media such as Iscove's Dulbecco's Modified Eagle's Medium or RPMI-1640 medium from Gibco, Grand Island, N.Y., or in vivo as ascites in laboratory animals. If desired, the antibody may be separated from the culture medium or body fluid, as the case may be, by conventional techniques such as ammonium sulfate precipitation, hydroxylapatite chromatography, ion exchange chromatography, affinity chromatography, electrophoresis, microfiltration, and ultracentrifugation.

The antibodies of this invention may be used passively to immunize individuals who suffer from *P. aeruginosa* septicemia or are at risk with respect to *P. aeruginosa* infection. Patients at risk include those receiving immunosuppressive therapy and those suffering from severe thermal burns or other serious injuries, cystic fibrosis and cancer.

Preferably two or more different antibodies, each of which recognizes and binds to a distinct serotype of the cell wall LPS, are employed.

In addition, a combination of one or more antibiotics and one or more serotype-specific mouse antibodies may be employed. Also, one or more type-specific monoclonal antibodies herein may be used in combination with one or more antibodies directed against the exotoxin A portion of *P. aeruginosa*. The antibodies may act synergistically in that the type-specific antibody may kill the organism and/or hasten its clearance while the exotoxin A-specific antibody may neutralize the toxin. The exotoxin A-specific antibodies may be prepared using the procedure described herein where the immunizing agent is exotoxin A or patients with high anti-exotoxin A titers are screened and an exotoxin A ELISA is employed. The procedure is more fully described in copending U.S. application entitled "Pseudomonas Aeruginosa Exotoxin A Monoclonal Antibodies, Their Preparation and Use" to J. Larrick et al. filed concurrently herewith as U.S. Ser. No. 727,514 on Apr. 26, 1985.

The antibodies may be administered to the patient by any suitable technique, including subcutaneous and parenteral administration, preferably parenteral. Examples of parenteral administration include intravenous, intraarterial, intramuscular and intraperitoneal, preferably intravenous. The dose and dosage regimen will depend mainly upon whether the antibody/antibodies is/are being administered for therapeutic or prophylactic purposes, the patient, and the patient's history. The total pharmaceutically effective amount of an antibody administered per dose will typically be in the range of about 0.2 to 20 mg/kg of patient body weight.

For parenteral administration the antibody/antibodies will generally be formulated in a unit dosage injectable form (solution, suspension, emulsion) in association with a pharmaceutically acceptable parenteral vehicle. Such vehicles are inherently nontoxic and nontherapeutic. Examples of such vehicles include water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances which enhance isotonicity and chemical stability, e.g., buffers and preservatives. The antibody will typically be formulated in such vehicles at a concentration of about 0.1 mg/ml to 100 mg/ml.

The various aspects of the invention are further described by the following examples, which are not intended to limit the invention in any manner. In these examples all percentages for solids are by weight and all percentages for liquids and gases are by volume unless otherwise noted, and all temperatures are given in degrees Celsius.

EXAMPLE I

Nine commercially obtained male balb/c mice were immunized once by intraperitoneal injection (200 μg/ml) of each of the nine heat-killed *P. aeruginosa* bacteria identified below. Four days after booster immunization by iv injection of the same dose of the bacteria or of 0.1 ml of Klebsiella Pneumonia ($2\times10^9$ organisms/ml) the mice were killed and their spleen cells were fused with mouse myeloma SP-2 obtained from the ATCC in Rockville, Maryland using 2.5–3.0×$10^8$ spleen cells and 1.5–3.0×$10^8$ SP-2 cells for each fusion.

The bacterial strains used to immunize the mice were all obtained from the ATCC and were as follows:

Strain B13 (serotype 1)
Strain PA220 (serotype 1)
Strain B14, LSY3632 (serotype 2)
Strain B15, 4490 (serotype 3)
Strain PA86 (serotype 3)
Strain B16, LSY3885 (serotype 4)
Strain B17, NNMeP32 (serotype 5)
Strain B18, 3972 (serotype 6)
Strain B19, LSY3779 (serotype 7)

The fusion mixture contained polyethylene glycol (PEG) 4000, 40% (w/v); and dimethylsulfoxide (DMSO), 10% (v/v) in Hank's balanced salt solution (HBSS)−/+ ($Ca^{2+}$free, 2 mM $MgSO_4$). Forty g of PEG 4000 was combined with 10 ml of DMSO and 50 ml of HBSS−/+. The mixture was autoclaved for 25 minutes. Before use, the pH of the fusion mixture was adjusted to 7.9 with sterile 0.1 N NaOH.

Plates (6 well cluster, 35 mm well diameter) were prepared as follows: 2 ml of HBSS−/+and 50 μl of a filter sterilized, 100 μg/ml peanut agglutinin (PNA, Sigma Chemicals) were added to each well. Plates were incubated at 37° C. for at least one hour prior to use. PNA stock was stored frozen, and a freshly thawed aliquot was used to coat fusion cells. Smaller sized wells were used if cell numbers were limited.

Parent cells were washed once or twice in HBSS−/+at room temperature and subsequently resuspended and combined at a ratio of about 1:1 splenocyte/SP-2 in HBSS−/+warmed to 37° C. Two ml of the combined cell suspension (10–20 million cells/well) was added to each pretreated well containing 1 μg/ml PNA coating solution. Plates were spun at 400–500×g at room temperature for five minutes to form a monolayer of cells. Supernatant was then aspirated off the plates.

Two ml of PEG fusion mixture described above and warmed to 37° C. was carefully added down the side of the fusion cell. After one minute, the PEG solution was diluted with a fusion dilution mixture (FDM) of 5% DMSO in HBSS−/+(filter sterilized and warmed to 37° C.) at a rate of 1 ml/15 sec. for up to 10 ml. The rest of the well was filled with HBSS−/+. The wells were aspirated and then each fusion well was washed twice with warm HBSS−/+and resuspended in 100 μl/well of an enriched hypoxanthine (EH) selection medium consisting of 100 μM hypoxanthine (Sigma) and Iscove's medium (Gibco), 10% NCTC (M.A. Biologicals), 20% heat-inactivated fetal bovine serum (FBS).

The next day 100 μl/well of EH and 4 μl/ml azaserine were added to give a final azaserine concentration of 2 μl/ml. The culture supernatants in wells where hybridomas grew were tested for antibodies to *P. aeruginosa* serotypes 1–7 by the ELISA method described below.

Fifty μl of 1.0% glutaraldehyde (Sigma) in deionized water was coated onto flat/bottom microtiter plates. After four hours of incubation at room temperature the wells were aspirated with an 8-channel manifold. Sixty μl of heptavalent *P. aeruginosa* vaccine (0.25% v/v) from Parke-Davis was added per well and incubated overnight. The plates were then washed with phosphate buffered saline (PBS) containing calcium and magnesium, and 0.05% surfactant from Sigma, and the plate bottom was blotted with soft tissue. Fifty μl of horseradish peroxidase conjugated goat anti-human Ig (Tago, Inc.) was then added to each well and the plate was incubated at 40° C. for 30 minutes. The wells were then washed as described above and blotted. Two-hundred μl ABTS substrate and 0.03% $H_2O_2$ were then added to each well and the plate was incubated at 37° C. for 30 minutes. The contents of the wells were transferred to a transparent plate and were read with an ELISA reader at 405 nm. Readings were reported on a scale of 1 to 10 with 1=0.0 OD, 10=2.0 OD.

The above technique was repeated using the nine immunizing strains described above instead of the heptavalent vaccine.

The hybridomas which recognized only one serotype of the seven were cultured in RPMI-1640 medium (Gibco) supplemented with 10% (vol/vol) FBS, and characterized.

Table I indicates the classes of antibodies which were expanded, their serotype specificity, and their isotypes, which were determined by the immunodiffusion method of Ouchterlony, *Prog. Allergy* (1962) 6:30–54 in PBS containing 0.85% agarose with rabbit antisera to mouse IgM, IgG and IgA (Miles Laboratories, Elkhart, Ind.).

TABLE I

Properties of Monoclonal Antibodies to *P. aeruginosa*

| Antibody | Serotype Specificity | Antibody Isotype |
|---|---|---|
| L108.13 | 1 | IgG |
| L108.16 | 1 | IgG |
| L108.19 | 1 | IgG |
| L108.11 | 1 | IgM |
| L113.5 | 2 | IgG |
| L113.15 | 2 | IgG |
| L113.11 | 2 | IgM |
| L109.4 | 3 | IgG |
| L109.8 | 3 | IgG |
| L110.1 | 4 | IgG |
| 1B6 | 5 | IgG |
| 6B11 | 5 | IgG |
| 6D12 | 5 | IgG |
| 17E1 | 6 | IgG |
| 10A5 | 6 | IgG |
| 11D7 | 6 | IgG |
| 6E11 | 6 | IgG |
| 9D11 | 6 | IgM |
| 18H6 | 7 | IgG |
| 10F2 | 7 | IgG |
| 16D10 | 7 | IgG |
| 9C8 | 7 | IgG |

Many of these antibodies were further subcloned. A sample of the hydridoma which produces a subcloned IgG antibody of serotype 1 was deposited at the American Type Culture Collection (ATCC), 12301 Parklawn Drive, Rockville, Md., USA. Deposit date and accession number are given below:

| Hybridoma | Deposit Date | Accession No. |
|---|---|---|
| L108.16.17 | 12 March 1985 | HB 8748 |

The deposit above was made pursuant to a contract between the ATCC and the assignee of this patent application, Cetus Corporation. The contract with ATCC provides for permanent availability of the progeny of this cell line to the public on the issuance of the U.S. patent describing and identifying the deposit or the publications or upon the laying open to the public of any U.S. or foreign patent application, whichever comes first, and for availability of the progeny of this cell line to one determined by the U.S. Commissioner of Patents and Trademarks to be entitled thereto according to 35 USC §122 and the Commissioner's rules pursuant thereto (including 37 CFR §1.14 with particular reference to 886 OG 638). The assignee of the present application has agreed that if the cell line on deposit should die or be lost or destroyed when cultivated under suitable conditions, it will be promptly replaced on notification with a viable culture of the same cell line.

Modifications of the above-described modes for carrying out the invention that are obvious to those of skill in the fields of hybridoma technology, immunology, bacterial infections, and related fields, are intended to be within the scope of the following claims.

What is claimed is:

1. A serotype-specific murine anti-Pseudomonas monoclonal antibody which binds to serotype 1 of *Pseudomonas aeruginosa* and is produced by hybridoma HB 8748.

2. The hybridoma designated as HB 8748.

* * * * *